United States Patent [19]

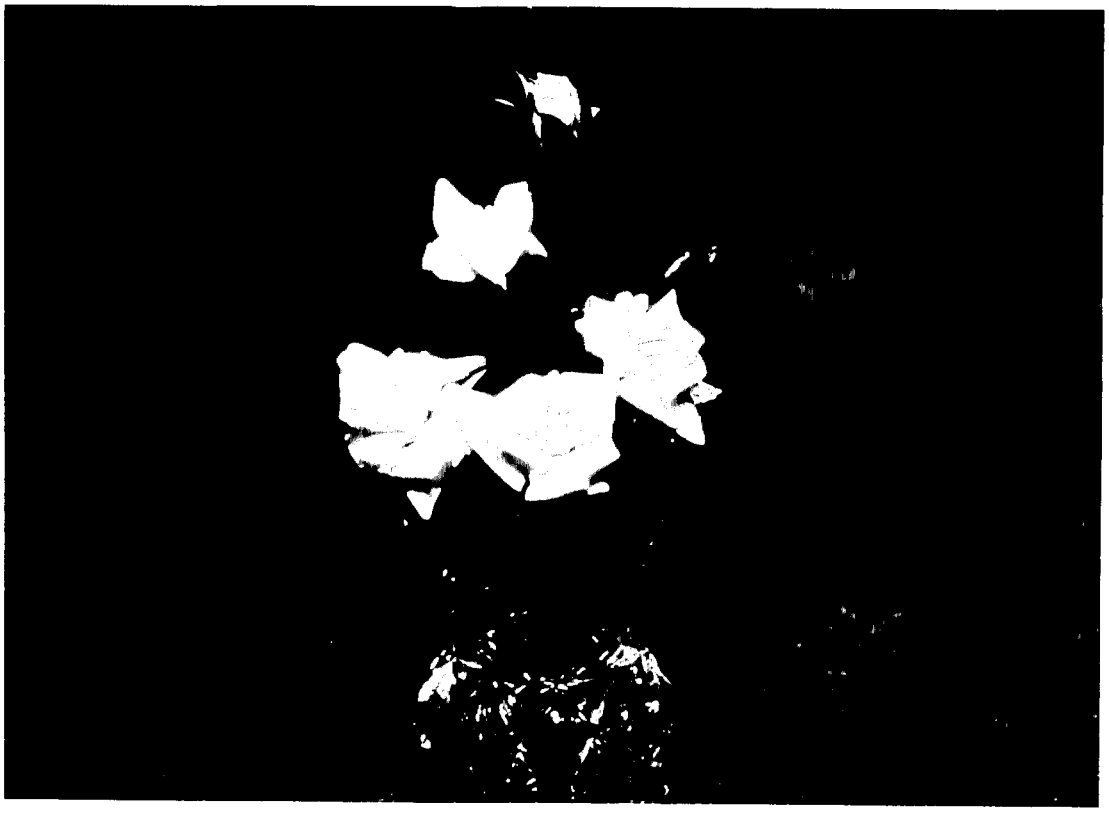

Bennett

[11] Patent Number: Plant 5,630

[45] Date of Patent: Jan. 14, 1986

[54] MINIATURE ROSE PLANT 'MEREDITH ANNE'

[76] Inventor: Cecilia L. D. Bennett, 489 Minot Ave., Chula Vista, Calif. 92010

[21] Appl. No.: 525,451

[22] Filed: Aug. 22, 1983

[51] Int. Cl.[4] ..... A01H 5/00

[52] U.S. Cl. ..... Plt./9

[58] Field of Search ..... Plt./9

*Primary Examiner*—James R. Feyrer

[57] ABSTRACT

The subject of the present disclosure is a new and distinct variety of miniature rose plant characterized by it's rich pink petals with soft pink under surface.

1 Drawing Figure

1

The present invention relates to a new and distinct variety of a hardy, dwarf, miniature bush plant of the miniature class; the variety being primarily characterized as a pink blend.

The variety is further characterized by:

Long stemmed exhibition-quality blooms, borne singly or in sprays, held very erect and well above the foliage.

Has a slight fragrance.

The plant ranges in height from 12 to 24 inches. The branches are sturdy and erect, heavily branched with medium foliage covering. The plant is a moderate bloomer that does well in either the hot house or outdoors.

The plant is vigorous, with good growing habits, well shaped and attractive in appearance, bearing numerous small leaflets.

The descriptive matter which follows pertains to roses grown and color values observed in plants and newly opened blooms in the months of May and June. The plants were grown outdoors in Chula Vista, Calif., and are believed to be accurate standards for this same cultivar in similar conditions of soil and climate elsewhere.

The seed parent was "Sonia" (U.S. Plant Pat. No. 3,095), and the pollen parent was "Tea Party" (R. S. Moore; introduced Sequoia Nursery, 1972).

Subsequent to the origination of the variety, I have successfully reproduced it at TINY PETAL'S NURSERY located at aforesaid retaining the distinguishing characteristics through succeeding propagations by cuttings.

The color photograph illustrates the variety.

Referring now specifically to the new and distinct variety of miniature rose plant, the following is a detailed description thereof in outline; all major color plate identifications being by reference to The British Colour Council Horticultural Colour Chart, except where common terms of color definition are employed.

Type: Hardy, dwarf, bushy, hot house or outdoor, garden decoration and exhibition-quality potted plant.

Class: Miniature.

Variety name: Meredith Anne.

Flowers borne: One to a stem or in sprays of 3 to 5 or more on erect stems with foliage well below the blooms.

Quantity of bloom: Abundant both outdoor and hot house grown.

Bud:

2

*Peduncle.*—Medium to short (averaging 20 to 25 mm); slender but sturdy; medium green with occasional tint of bronze.

*Hairs.*—Extremely small and delicate at short intervals along the peduncle only.

*Calyx.*—Color — Pod Green (061/1 page 120) from the base of the calyx tube to approximately the middle of sepals, with the top portion of the calyx heavily tinted with bronze.

*Opening.*—Opens well in all weather.

Bloom:

*Size when fully open.*—Average for a miniature variety 40 to 45 mm ($1\frac{3}{4}$").

*Petalage.*—Double — Averaging about 26 petals, arranged regularly plus numerous small petaloids.

*Form.*—Urn-shaped to ovoid as the bloom progresses. The petals remain at first somewhat tightly cupped with the tips and/or margins reflexed outward, becoming later at maturity more loosely cupped, with tips and/or margins reflexed outward.

Petals: Fairly thick with good substance, the inside surface being slightly satiny and the outside surface being slightly matte.

*Shape.*—Outer petals are of a broad obovate form with a slight peak at the apex. The intermediate petals are very much like the outer petals only narrower. The inner petals are more like broad lanceolates, and the petaloids are very small lanceolates.

Color: Newly opened flowers from plants grown outdoors (May and June 1983), Chula Vista, Calif.

*Outside petals.*—Upper surface — Camellia Rose (622/1 page 148) gradually lightening to Camellia Rose (622/2 page 148) with a small area at the base of Naples Yellow (403 page 121). Under surface — Camellia Rose (622/2 page 148) gradually lightening to Camellia Rose (622/3 page 148) with a small area at the base of Naples Yellow (403 page 121).

*Intermediate petals.*—Upper surface — Similar to outside petals. Under Surface — Similar to outside petals.

*Inner petals.*—Upper Surface — Scarlet (19/2 page 19) with a small area at the base of Chrome Yellow (605/1 page 144). Under Surface — Scarlet (19/2 page 19) gradually lightening to Scarlet (19/3 page 19) with a small area at the base of Chrome Yellow (605/1 page 144).

*General color effect.*—Newly opened flowers — rich pink with a deeper tone slightly visible toward the center of the bloom. Two days open — Color slightly paler than newly opened. Spents petals drop off cleanly, except petaloids.

*Flower longevity.*—(May and June 1983) Plant in pot 6 to 8 days from bud with sepals down to fully open bloom. Holding at fully open with only slight fading of color for additional 3 to 4 days before dropping petals. Cut blooms at livingroom temperature 4 to 5 days or longer.

Reproductive Organs:

*Stamens.*—A generous amount arranged uniformly around the pistil, with a few among the petaloids.

*Filament.*—Varying in lengths.

*Pollen.*—Abundant.

*Pistil.*—Short, abundant and spreading.

*Styles.*—Short and irregular.

*Ovaries.*—All encased in calyx.

*Hips.*—Some.

*Seed.*—Few or none.

*Sepals.*—Permanent; spear-shaped; recurved against peduncle.

Foliage:

*Leaves.*—Five to seven, small in size.

*Leaflets.*—Broad ovate-shaped.

*Margin.*—Very serrated with a reddish tinge on the edge of the most of the leaflets.

*Color.*—Ranging from Scheeles Green (860/2 page 175) in the newest leaflets to Spinach Green (0960/2 page 187) in the mature leaflets.

*Rachis.*—Medium strength; upper side may have a few tiny hairs, grooved; underside smooth except for a few sparse thorns.

*Stipules.*—Varying in length from short to medium; narrow to medium width; tapering auricles angled outward at about 45 degrees.

Growth:

*Habit.*—Dwarf; bushy; rounded; much branched.

*Growth.*—Vigorous.

*Canes.*—Medium; slender; sturdy.

*Main stems.*—Color — Spinach Green (0960/2 page 187) with some tinting of bronze.

*Thorns.*—Average; slender; hooked slightly downward; color — varying from brown to pale yellow. Prickles — none. Hairs — Present only sparsely on the upper part of the rachis and on the peduncle.

*Branches.*—Color — Spinach Green (0960/2 page 187) with some tinting of bronze. Medium length; slender; sturdy. Thorns — Usually only one located just below each leaflet or midway between the leaflets; hooked slightly downward. Prickles — None. Hairs — None.

The miniature rose plant and its flowers as herein described may vary in slight detail due to climatic, soil and cultural conditions under which the variety may be grown; the present description being of the variety as grown at Chula Vista, Calif.

The following is claimed:

1. A new and distinct variety of miniature rose plant of hardy, dwarf, bushy, much branched habit, substantially as illustrated and described, characterized by rich pink color in the petals with soft pink under surfaces, having a bloom of exhibition-quality form; and further characterized by a plant of vigorous growth habit, easy to propagate from cuttings, with an abundance of flowers borne singly or in sprays of usually 3 to b 5 or more.

* * * * *